United States Patent [19]

Teraji et al.

[11] 4,382,934
[45] May 10, 1983

[54] ISATIN DERIVATIVES, PROCESSES FOR THE PREPARATION THEREOF AND PHARMACEUTICAL COMPOSITION COMPRISING THE SAME

[75] Inventors: Tsutomu Teraji; Teruo Oku, both of Osaka; Takayuki Namiki, Ikeda, all of Japan

[73] Assignee: Fujisawa Pharmaceutical Co., Ltd., Osaka, Japan

[21] Appl. No.: 83,271

[22] Filed: Oct. 10, 1979

[30] Foreign Application Priority Data

Oct. 10, 1978 [GB] United Kingdom ............ 39977/78

[51] Int. Cl.³ .................. A61K 31/495; C07D 403/06
[52] U.S. Cl. ............................. 424/250; 424/248.56; 424/248.57; 424/263; 424/267; 424/273 R; 260/239 BC; 260/243.3; 260/244.4; 260/245.5; 544/121; 544/129; 544/130; 544/139; 544/143; 544/364; 544/370; 544/144; 544/373; 544/357; 546/273; 544/360; 548/336
[58] Field of Search ............... 544/121, 129, 130, 139, 544/143, 144, 357, 360, 370, 373; 260/239 BC, 244.4, 243.3, 245.5; 546/273; 548/336; 424/248.56, 248.57, 250, 263, 267, 273 R

[56] References Cited
U.S. PATENT DOCUMENTS 2,909,523 10/1959 Bach, Jr. et al. ............... 544/373
3,632,587 1/1972 Hollowood ..................... 544/373

FOREIGN PATENT DOCUMENTS 2012667 10/1970 Fed. Rep. of Germany .
49-10671 of 1974 Japan .
1240648 7/1971 United Kingdom .
1326833 8/1973 United Kingdom .
1382916 2/1975 United Kingdom .

Primary Examiner—Donald G. Daus

Assistant Examiner—James H. Turnipseed
Attorney, Agent, or Firm—Oblon, Fisher, Spivak, McClelland & Maier

[57] ABSTRACT

A compound of the general formula:

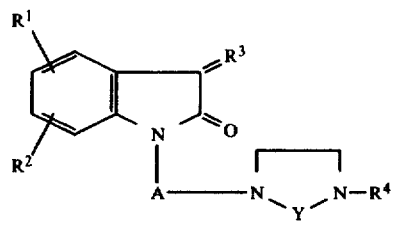

wherein
$R^1$ and $R^2$ are hydrogen, halogen, lower alkyl, lower alkoxy, halo (lower) alkyl, lower alkanoylamino, lower alkoxyalylamino, or a 5 to 6 membered saturated or unsaturated heterocyclic group having at least one imino group, and selected from the group consisting of pyrrolidinyl, pyrrolinyl, imidazolidinyl, piperazinyl, piperidyl, and morpholynyl, or $R^1$ and $R^2$ are combined together to form a benzene ring,
$R^3$ is oxo or a group of the formula $=N-OR^5$, in which $R^5$ is hydrogen or lower alkyl,
$R^4$ is mono- or di- or triphenyl (lower) alkyl,
A is $C_1$ to $C_7$ alkylene and its hydroxy derivatives,
Y is ($C_1$ to $C_3$) alkylene,
or a pharmaceutically acceptable salt thereof.

Said compounds having antiallergic properties represent inclusively all of the possible optical and/or geometrical isomers due to the asymmetric carbon and carbon-nitrogen double bond.

16 Claims, No Drawings

ISATIN DERIVATIVES, PROCESSES FOR THE PREPARATION THEREOF AND PHARMACEUTICAL COMPOSITION COMPRISING THE SAME

The present invention relates to new isatin derivatives and pharmaceutically acceptable salts thereof. More particularly, it relates to new isatin derivatives and pharmaceutically acceptable salts thereof which have antiallergic activities, to processes for the preparation thereof, to pharmaceutical composition comprising the same, and to a method of using the same therapeutically in the treatment of allergic symptoms in human being and animals.

Accordingly, it is one object of the present invention to provide isatin derivatives and pharmaceutically acceptable salts thereof, which are useful as antiallergic agents.

Another object of the present invention is to provide processes for the preparation of isatin derivatives and pharmaceutically acceptable salts thereof.

A further object of the present invention is to provide pharmaceutical composition comprising, as active ingredients, said isatin derivatives or pharmaceutically acceptable salts thereof.

Still further object of the present invention is to provide a method of using said isatin derivatives or pharmaceutically acceptable salts thereof, for the treatment of allergic symptoms in human being and animals.

The object isatin derivatives of the present invention are novel and can be represented by the following formula (I):

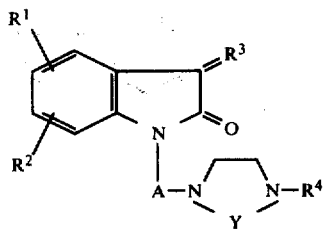

wherein
$R^1$ and $R^2$ are each hydrogen, halogen, lower alkyl, lower alkoxy, halo(lower)alkyl, acylamino, or heterocyclic group containing at least one imino group, or
$R^1$ and $R^2$ are combined together to form a benzene ring,
$R^3$ is oxo or a group of the formula: =N—OR$^5$ in which $R^5$ is hydrogen or lower alkyl,
$R^4$ is hydrogen; ar(lower)alkyl optionally having halogen, carboxy or esterified carboxy; aryl optionally having halogen; acyl; or 10,11-dihydro-5H-dibenzo[a,d]cycloheptenyl;
A is lower alkylene optionally having hydroxy, and
Y is ($C_1$ to $C_3$)alkylene With regard to the object compound of the above formula (I), it is to be understood that the compound (I) represents inclusively all of the possible optical and/or geometrical isomers due to the asymmetric carbon atom and carbon-nitrogen double bond (>C=N—) in the molecule of the compound (I), and accordingly such optical and/or geometrical isomers are also included within the scope of the present invention.

As to the various definitions as indicated above, suitable illustrations and examples are explained in detail as follows.

The term "lower" is intended to mean 1 to 6 carbon atom(s), unless otherwise indicated.

Suitable "halogen" for $R^1$ and $R^2$, and "halogen" as the substituent for ar(lower)alkyl and aryl for $R^4$ may include fluorine, chlorine, bromine and iodine, in which the preferred one is fluorine, chlorine and bromine.

Suitable "lower alkyl" for $R^1$, $R^2$ and $R^5$ may include straight and branched chain one such as methyl, ethyl, propyl, isopropyl, butyl, isobutyl, tert-butyl, pentyl, hexyl and the like, in which the preferred one is $C_1$-$C_4$alkyl.

Suitable "lower alkoxy" for $R^1$ and $R^2$ may include straight and branched chain one such as methoxy, ethoxy, propoxy, isopropoxy, butoxy, isobutoxy, pentyloxy, hexyloxy and the like, in which the preferred one is $C_1$-$C_3$alkoxy.

Suitable "halo(lower)alkyl" for $R^1$ and $R^2$ may include mono(or di or tri)halo(lower)alkyl (e.g. chloromethyl, dibromomethyl, trifluoromethyl, dichloroethyl, etc.) and the like, in which the preferred one is trihalo($C_1$-$C_3$)alkyl.

Suitable "acyl" moiety in the term "acylamino" for $R^1$ and $R^2$, and "acyl" group for $R^4$ may include:
lower alkanoyl (e.g. formyl, acetyl, propionyl, butyryl, isobutyryl, valeryl, isovaleryl, oxalyl, succinyl, pivaloyl, etc.);
lower alkoxalyl (e.g. methoxalyl, ethoxalyl, propoxalyl, etc.);
N,N-diarylcarbamoyl (e.g. diphenylcarbamoyl, ditolylcarbamoyl, dixylylcarbamoyl, etc.);
and the like.

Suitable "heterocyclic group containing at least one imino group" for $R^1$ and $R^2$ may include 5- or 6-membered saturated or unsaturated heterocyclic group containing at least one imino group (>N—H) and optionally nitrogen, oxygen and/or sulfur atom(s), examples of which may be pyrrolidinyl, pyrrolinyl, imidazolidinyl, piperazinyl, piperidyl, morpholynyl and the like, in which the preferred one is 6-membered saturated heterocyclic-N-yl group containing one imino group and one oxygen atom (e.g. morpholino, etc.).

Suitable "ar(lower)alkyl optionally having halogen, carboxy or esterified carboxy" for $R^4$ may include:
mono(or di or tri)phenyl(lower)alkyl (e.g. benzyl, phenethyl, benzhydryl, trityl, etc.); p1 mono(or di or tri)phenyl(lower)alkyl having 1 to 5 halogen atom(s) as exemplified for $R^1$ and $R^2$ on the phenyl ring thereof (e.g. chlorobenzyl, bromobenzyl, fluorobenzyl, chlorophenethyl, dichlorobenzyl, trichlorobenzyl, tetrachlorobenzyl, pentachlorobenzyl, etc.);
mono(or di or tri)phenyl(lower)alkyl having carboxy or esterified carboxy (e.g. lower alkoxycarbonyl etc.) on the alkyl moiety thereof (e.g. α-carboxybenzyl, α-methoxycarbonylbenzyl, α-ethoxycarbonylbenzyl, α-propoxycarbonylbenzyl, etc.); in which preferred carbon number of the alkyl moiety is 1 to 3.

Of the suitable examples as mentioned above, the more preferred ones are selected from the group consisting of monophenyl($C_1$-$C_3$)alkyl, diphenyl($C_1$-$C_3$)alkyl and triphenyl($C_1$-$C_3$)alkyl, each of which optionally has 1 to 3 (preferably 1) halogen atom (preferably chlorine) on the phenyl moiety thereof, and monophenyl($C_1$-$C_3$)alkyl of which has carboxy or esterified carboxy on the alkyl moiety thereof, and the most preferred ones are benzhydryl, trityl, halobenzyl (e.g. chlorobenzyl, etc.) and α-carboxy-or α-lower alkoxy-carbonylbenzyl (e.g. α-methoxycarbonylbenzyl, etc.).

Suitable "aryl optionally having halogen" for R⁴ may include phenyl, tolyl, naphthyl, phenyl having 1 to 5 halogen atom(s) as exemplified for R¹ and R² (e.g. chlorophenyl, bromophenyl, dichlorophenyl, trichlorophenyl, tetrachlorophenyl, pentachlorophenyl, etc.), and the like, in which the preferred one is phenyl optionally having 1 to 3 (preferably 1) halogen atom(s) (preferably chlorine) such as chlorophenyl (e.g. 3- or 4-chlorophenyl, etc.).

Suitable "lower alkylene optionally having hydroxy" for A may include straight or branched lower alkylene (e.g., methylene, ethylene, trimethylene, propylene, tetramethylene, ethylethylene, pentamethylene, hexamethylene, etc.) and straight or branched lower alkylene having hydroxy (e.g. 2-hydroxytrimethylene, 2- or 3-hydroxytetramethylene, 2-,3- or 4-hydroxyhexamethylene, etc.), in which the preferred one is $C_2$-$C_7$alkylene optionally having a hydroxy group, and the more preferred one is $C_2$-$C_5$alkylene optionally having a hydroxy group.

Suitable "($C_1$ to $C_3$)alkylene" for Y may include methylene, ethylene, propylene, trimethylene and the like, and the most preferred one is ethylene, where the partial formula:

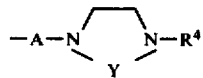

can be represented by the formula:

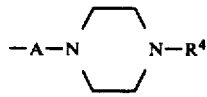

Suitable pharmaceutically acceptable salts of the object compounds (I) are conventional non-toxic salts and may include:
- an acid addition salt such as an inorganic acid addition salt (e.g. hydrochloride, hydrobromide, sulfate, phosphate, etc.), an organic acid addition salt (e.g. oxalate, maleate, lactate, tartrate, methanesulfonate, benzenesulfonate, toluenesulfonate, etc.) or a salt with an amino acid (e.g. aspartic acid, glutamic acid, etc.);
- lower alkylated quaternary ammonium salt such as lower alkyl ammonium halide (e.g. methylammonium iodide, etc.), lower alkylammonium lower alkylsulfate (e.g. methylammonium methylsulfate, etc.), or lower alkylammonium hydroxide (e.g. methylammonium hydroxide, etc.);
- salt with a base such as alkali metal salt (e.g. sodium salt, potassium salt, etc.);

and the like.

The definition of "R¹ and R² are combined together to form benzene ring" can more particularly be represented by the definition of "R¹ and R², when both of them, are combined to form a benzene ring as represented by the partial formula:

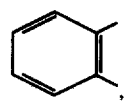

in which R¹ and R² are positioned, for example, at 4th and 5th positions of isatin nucleus, 5th and 6th ones or 6th and 7th ones, respectively, the isatin nucleus being represented by the formula:

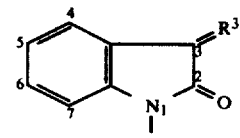

The object compounds (I) of the present invention can be prepared by the following processes.

Process 1:

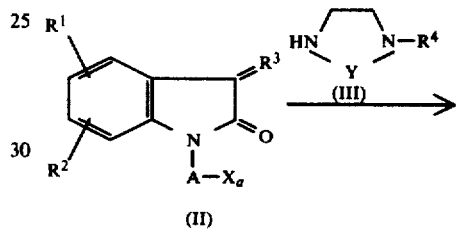

Process 2:

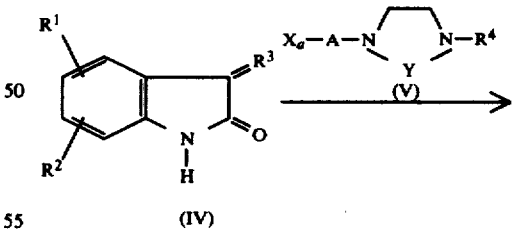

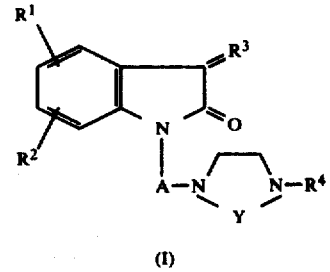

Process 3:

-continued
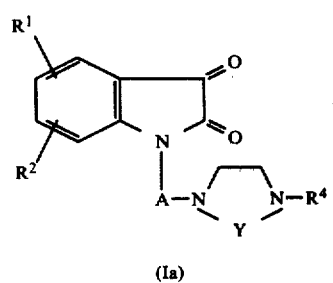
(Ia)
H₂N—OR⁵ (VI) →
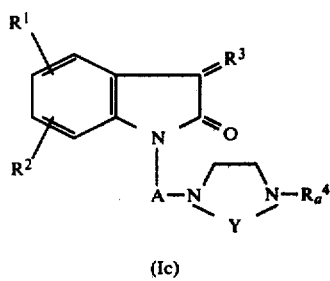
(Ib)
Process 4:
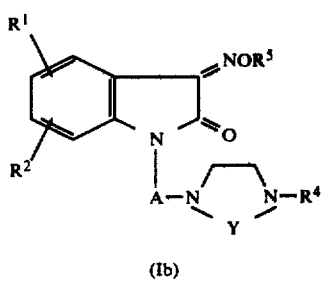
(Ic)
Elimination of the ar(lower) alkyl group →
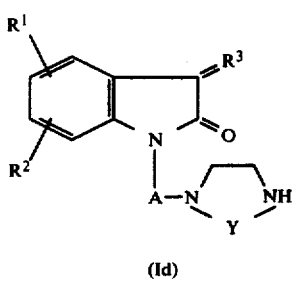
(Id)
Process 5:
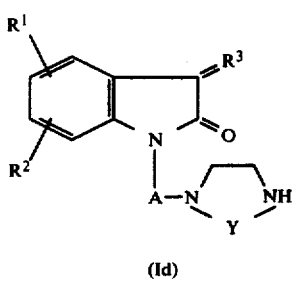
(Id)
R_b⁴—OH (VII) →
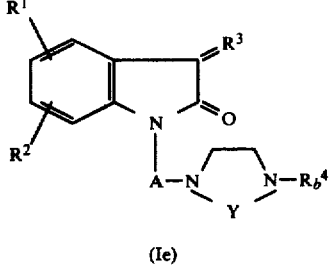
(Ie)
Process 6:
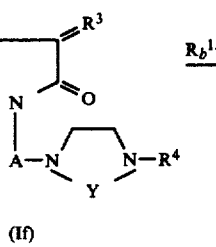
(If)
R_b¹—H (VIII) →
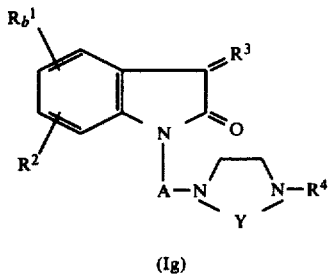
(Ig)
Process 7:
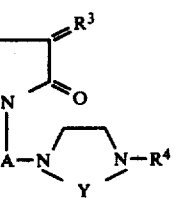
(I)
R⁶—X_b (IX) →
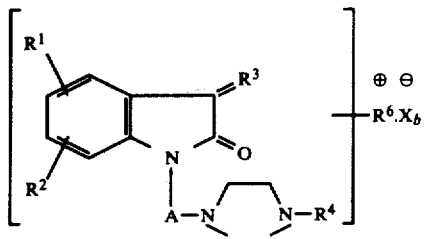
(Ih)
Wherein
R¹, R², R³, R⁴, R⁵, A and Y are each as defined above.
R_a¹ is halogen,
R_b¹ is a heterocyclic-N-yl group containing at least one imino group, $R_a^4$ is ar(lower)alkyl, $R_b^4$ is ar(lower)alkyl having esterified carboxy on the alkyl moiety thereof, acyl or 10,11-dihydro-5H-dibenzo[a,d]cycloheptenyl, $R^6$ is lower alkyl, $X_a$ is an acid residue, and $X_b$ is halogen or lower alkoxysulfonyloxy.

Suitable examples of "halogen" for $R_a^1$; "heterocyclic-N-yl group containing at least one imino group" for $R_b^1$; "ar(lower)alkyl" for $R_a^4$; and "ar(lower)alkyl having esterified carboxy on the alkyl moiety thereof" and "acyl" for $R_b^4$ are the same as those as illustrated and exemplified for the corresponding groups of $R^1$, $R^2$ and $R^4$, respectively.

Suitable "lower alkyl" for $R^6$ may be the same ones as illustrated and exemplified for $R^1$ and $R^2$.

Suitable "acid residue" for $X_a$ may include halogen (e.g. chlorine, bromine, iodine, etc.), azido, acyloxy (e.g. benzenesulfonyloxy, tosyloxy, etc.) and the like.

Suitable "halogen" for $X_b$ may be the same ones as illustrated and exemplified for $R^1$ and $R^2$.

The aforementioned processes for preparing the object compound (I) of the present invention are explained in detail in the following.

Process 1

The compound (I) and it salt can be prepared by reacting a compound (II) with a compound (III) or its salt.

Suitable salt of the compound (III) may be an acid addition salt as exemplified before.

This reaction can preferably be carried out in the presence of an organic or inorganic base such as tri(-lower)alkylamine (e.g. trimethylamine, triethylamine, etc.), N,N-di(lower)alkyl arylamine (e.g. N,N-dimethylaniline, etc.), N,N-di(lower)alkyl ar(lower)alkylamine (e.g. N,N-dimethyl benzylamine, etc.), pyridine, picoline, 1,5-diazabicyclo[4,3,0]non-5-ene, 1,4-diazabicyclo[2,2,2]octane, 1,5-diazabicyclo[5,4,0]undecene-5, alkali metal acetate (e.g. sodium acetate, potassium acetate, etc.), alkali metal lower alkoxide (e.g. sodium methoxide, sodium ethoxide, potassium tert-butoxide, etc.), alkali metal hydride (e.g. sodium hydride, potassium hydride, etc.), alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate potassium bicarbonate, etc.), or the like.

This reaction can also be carried out in the presence of a reaction stimulator such as metal halide (e.g. sodium iodide, potassium iodide, etc.) or the like.

This reaction is usually carried out in a conventional solvent such as methanol, benzene, acetone, dioxane, N,N-dimethylformamide or any other solvent which does not adversely influence the reaction.

This reaction temperature is not critical and the reaction is usually carried out under warming or heating.

Process 2

The compound (I) and its salt can be prepared by reacting a compound (IV) or its salt with a compound (V) or its salt.

Suitable salt of the compound (IV) may be a salt with base and suitable salt of the compound (V) may be an acid addition salt as exemplified before, respectively.

This reaction can be carried out in substantially the same manner as that of Process 1, and therefore the reaction mode and reaction conditions (e.g. base, solvent, reaction temperature, etc.) for this reaction are to be referred to those as explained in Process 1.

Process 3

The compound (Ib) and its salt can be prepared by reacting a compound (Ia) or its salt with a compound (VI) or its salt.

Suitable salt of the compound (VI) may be an acid addition salt as exemplified before.

This reaction can be carried out in the presence of a base as exemplified in Process 1.

This reaction is usually carried out in a conventional solvent such as water, lower alkanol (e.g. methanol, ethanol etc.) and any other solvent which does not adversely influence the reaction.

This reaction temperature is not critical and the reaction is usually carried out under cooling or at ambient temperature or under heating.

Process 4

The compound (Id) and its salt can be prepared by subjecting a compound (Ic) or its salt to removal reaction of the ar(lower)alkyl group for $R_a^4$.

Suitable method for this elimination reaction may include hydrolysis, hydrogenolysis, and the like.

In case that the elimination reaction is conducted by hydrolysis, the hydrolysis is preferably carried out in the presence of an acid.

Suitable acid may include an inorganic acid (e.g. hydrochloric acid, hydrobromic acid, sulfuric acid, etc.), an organic acid (e.g. formic acid, acetic acid, trifluoroacetic acid, propionic acid, benzenesulfonic acid, p-toluenesulfonic acid, etc.), and the like.

The hydrolysis is usually carried out in a conventional solvent such as water, methanol, ethanol, tetrahydrofuran, dioxane, N,N-dimethylformamide or any other solvent which does not adversely influence the reaction.

The reaction temperature is not critical and the reaction is usually carried out at ambient temperature.

In case that the elimination reaction is conducted by hydrogenolysis, hydrogenolysis is carried out by conventional catalytic reduction, and suitable catalyst may be palladium catalyst (e.g. palladium on charcoal, palladium on barium sulfate, colloidal palladium, spongy palladium, etc.), platinum catalyst (e.g. platinum plate, platinum wire, platium black, spongy platinum, etc.), and the like.

The catalytic reduction is usually carried out in a conventional solvent such as water, methanol, ethanol, propanol or any other solvent which does not adversely influence the reaction.

The reaction temperature is not critical and the reaction is usually carried out at ambient temperature or under warming.

Process 5

The compound (Ie) and its salt can be prepared by reacting a compound (Id) or its salt with a compound (VII) or its reactive derivative at the hydroxy group thereof.

The suitable "reactive derivative" at the hydroxy group of the compound (VII) may be a halide (e.g. chloride, bromide, etc.).

This reaction is preferably carried out in the presence of a base as exemplified in Process 1.

In this reaction, the starting compound (Id) can be used in the activated form at the imino group of the partial structure $$-A-N\underset{Y}{\overset{}{\diagup\!\!\!\diagdown}}N-H$$

of the compound (Id), and such activated form may include a conventional one, for example, a silyl derivative formed by the reaction of the compound (Id) with a silyl compound such as trimethylsilylacetamide, bis(-trimethylsilyl)acetamide, and the like.

In case that the starting compound (VII), wherein $R_b^4$ is acyl, of this reaction is used in a form of free hydroxy group, the reaction can preferably be carried out in the presence of a condensing agent such as a carbodiimide compound (e.g., N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.), a ketenimine compound (e.g., N,N'-carbonylbis(2-methylimidazole), pentamethyleneketene-N-cyclohexylimine, diphenylketene-N-cyclohexylimine, etc.); an olefinic or acetylenic ether compound (e.g., ethoxyacetylene), β-chlorovinylethyl ether, a sulfonic acid ester of N-hydroxybenzotriazole derivative (e.g., 1-(4-chlorobenzenesulfonyloxy)-6-chloro-1H-benzotriazole, etc.), a phosphorus compound (e.g., trialkyl phosphite, ethyl polyphosphate, isopropyl polyphosphate, phosphoryl chloride, phosphorus trichloride, triphenylphosphine, etc.), thionyl chloride, oxalyl chloride, N-ethylbenzisoxazolium salt, N-ethyl-5-phenylisoxazolium-3'-sulfonate, a reagent (referred to as so-called "Vilsmeier reagent") formed by the reaction of an amide compound (e.g. dimethylformamide, dimethylacetamide, N-methylformamide, etc.) with a halogen compound (e.g. thionyl chloride, phosphoryl chloride, phosgene, etc.), and the like.

This reaction is usually carried out in a conventional solvent such as methylene chloride ethylene chloride, acetone, methanol, ethanol, N,N-dimethylformamide or any other solvent which does not adversely influence the reaction.

The reaction temperature is not critical and the reaction is usually carried out under cooling or at ambient temperature.

Process 6

The compound (Ig) and its salt can be prepared by reacting a compound (If) or its salt with a compound (VIII) or its salt.

Suitable salt of the compound (VIII) may be an acid addition salt as exemplified before.

This reaction can be carried out in substantially the same manner as that of Process 1, and therefore the reaction mode and reaction conditions (e.g. base, solvent, reaction temperature, etc.) for this reaction are to be referred to those as explained in Process 1.

Process 7

The compound (Ih) can be prepared by reacting a compound (I) with a compound (IX).

This reaction can be carried out in a conventional manner which can be applied to preparation of so-called quarternary ammonium salt.

This reaction is usually carried out in a conventional solvent such as methanol, ethanol, propanol or any other solvent which does not adversely influence the reaction.

The reaction temperature is not critical and the reaction is usually carried out at ambient temperature or under heating.

It is to be noted that in case that the reaction is carried out in the presence of an excess amount of the compound (IX), disalt of the compound (IX) can frequently be obtained, and such case is included within the scope of this process.

Further, in case that the object compound (Ih) is treated with anion exchange resin (OH⁻ form), or metal oxide or its hydrate (e.g. silver oxide, etc.), the compound (Ih), wherein $X_b$ is as defined above, is transformed into the compound (Ih), wherein $X_b$ is hydroxy, and such case is included within the scope of this process.

The object compound (I) obtained in the above Processes 1 to 7 can be isolated and purified in a conventional manner, for example, extraction, precipitation, fractional chromatography, fractional crystallization, recrystallization, and the like.

The object compound (I) thus prepared can be transformed into optional pharmaceutically acceptable salt by a conventional method, if desired.

The starting compounds (II) and (V) are novel and can be prepared by the following processes.

Process A:

$$\underset{(IV)}{R^1\!\!-\!\!\!\text{indolinone}\!\!=\!\!R^3} \xrightarrow{X'-A-X_a \ (X)} \underset{(II)}{R^1\!\!-\!\!\!\text{indolinone}\!\!=\!\!R^3, N-A-X_a}$$

Process B:

$$H-N\underset{Y}{\overset{}{\diagup\!\!\!\diagdown}}N-R^4 \xrightarrow{X'-A-X_a \ (X)} X_a-A-N\underset{Y}{\overset{}{\diagup\!\!\!\diagdown}}N-R^4$$

(III)                               (V)

Wherein $R^1$, $R^2$, $R^3$, $R^4$, A, $X_a$ and Y are each as defined above, and X' is an acid residue.

Suitable "acid residue" for X' may be the same ones as those as illustrated and exemplified for $X_a$.

The processes for preparing the starting compounds are explained in detail in the following.

Process A

The compound (II) can be prepared by reacting a compound (IV) with a compound (X). This reaction can be carried out in substantially the same manner as that illustrated in Process 1, and therefore, the reaction mode and reaction conditions (e.g. base, solvent, reaction temperature, etc.) for this reaction are to be referred to those as explained in Process 1.

Process B

The starting compound (V) and its salt can be prepared by reacting a compound (III) or its salt with a compound (X).

This reaction can be carried out in substantially the same manner as that illustrated in Process 1, and therefore, the reaction mode and reaction conditions (e.g. base, solvent, reaction temperature, etc.) for this reaction are to be referred to those as explained in Process 1.

The object compound (I) and pharmaceutically acceptable salts thereof obtained according to the processes of this invention have potent and long lasting antiallergic activity and can be used therapeutically as well as prophylactically as antiallergic agents for relieving or inhibiting allergic symptoms of human being and animals.

Test Compound

1-[3-(4-Benzhydryl-1-piperazinyl)propyl]isatin

Test Method (1) Preparation of rabbit antiserum against egg albumin

Equal volumes of a saline solution of egg albumin (200 mg./ml.) and of Freund's Complete Ajuvant were mixed and emulsified. Each male New Zealand white strain rabbits, each weighing 2 to 2.5 kg., received an intramuscular injection of 0.5 ml. of the emulsion in the left and right thigh regions. One week later, they received an intradermal injection of 0.25 ml. of a saline solution of egg albumin (concentration: 20 mg./ml.) in the different four sites of the dorsal skin surface three times every other week. Blood samples were collected from the carotid artery one week after the last injection.

(2) Determination of Passive Cutaneous Anaphylaxis (PCA) titer

The level of anaphylactic anti-egg albumin antibodies in pools of sera were determined by passive cutaneous anaphylaxis (PCA) reactions using shaven Hartley strain test guinea-pigs.

Antiserum was serially diluted (two fold) in saline and 0.1 ml. of each antiserum dilution were injected intradermally into the dorsal skin surface of the test guinea-pigs. 24 Hours after intradermal sensitization, Egg albumin-specific PCA reactions were elicited by intravenous injection of 10 mg. of egg albumin in 1 ml. of 1% Evans blue dye dissolved in saline. Reactions were read and recorded as the highest dilution of serum evoking threshold PCA reactivity (5 mm diameter).

(3) Antagonism to anaphylactic asthma in guinea-pigs

Male Hartley stain guinea-pigs, weighing 305 to 400 g, were used. Animals were sensitized by an intravenous injection of rabbit antiserum against egg albumin (4000 PCA titer) with 0.5 ml./animal. After 24 hours, animals were placed individually in a plastic chamber of 5.3 liter volume. An aerosol of 5% egg albumin solution was sprayed in the chamber at a rate of 0.16 ml./min with a commercial nebulizer. The test compound was given to the animals orally 30 minutes before the challenge with the egg albumin solution. Each dose group consisted of ten animals. The inhibitory effect of the test compound was determined from the number of surviving animals more than 2 hours after spray of the antigen. The $ED_{50}$ value (dose to be required 50% protection from death) was calculated according to Litchfield-Wilcoxon method.

Test Results

| Inhibitory effect of anaphylactic asthma in guinea-pig | |
|---|---|
| Dose (mg./kg.) P.O. | Inhibitory effect (%) |
| 0.1 | 0 |
| 1.0 | 20 |
| 3.2 | 40 |
| 10.0 | 80 |
| 32.0 | 100 |
| 100.0 | 100 |
| $ED_{50}$ (m.g./kg.) | 3.4 |

As being apparent from the above test results, the object compound (I) of the present invention are useful for the antiallergic medicines.

For therapeutic administration, the object compound (I) of the present invention and pharmaceutically acceptable salts thereof are used in a form of the conventional pharmaceutical preparation in admixture with a conventional pharmaceutically acceptable carrier such as an organic or inorganic solid or liquid excipient which is suitable for oral, parenteral or external administration. The pharmaceutical preparation may be compounded in a solid form such as capsule, tablet, dragee, ointment or suppository, or in a liquid form such as solution, suspension or emulsion. If needed, there may be included in the above preparation auxiliary substance, stabilizing agent, wetting or emulsifying agent, buffer or any other commonly used additives.

The effective ingredient may usually be administered with a unit dose of 1 mg./kg. to 500 mg./kg., 1 to 4 times a day. However, the above dosage may be increased or decreased according to age, weight, conditions of the patient or the administering method.

The following examples are given only for the purpose of illustrating the present invention in more detail.

PREPARATION OF THE OBJECT COMPOUNDS

Example 1

A mixture of 1-(3-chloropropyl)isatin (13.44 g), 1-benzhydrylpiperazine (19.92 g), triethylamine (7.2 g) and potassium iodide (9.96 g) in N,N-dimethylformamide (144 ml) was stirred for 1.5 hours at 80° to 85° C. The reaction mixture was cooled, poured into a cold aqueous solution of sodium bicarbonate and extracted with ethyl acetate. The extract was washed with water, dried over anhydrous magnesium sulfate and evaporated. The residue was dissolved in chloroform and subjected to column chromatography on silica gel (60 g) using chloroform as an eluent. The eluate was evaporated, and the remaining oil was dissolved in ethanol (160 ml). To a solution was added 29% ethanolic hydrogen chloride (30 ml) under cooling or an ice bath, and the resultant mixture was stirred for 10 minutes. The precipirated crystals were collected by filtration and then dried to give 1-[3-(4-benzhydryl-1-piperazinyl)propyl]isatin dihydrochloride (20.17 g). Thus obtained product was purified by recrystallization from 92% ethanol (410 ml) to give the purified product of the same compound (10.44 g), mp. 245° to 248° C. (dec.).

I.R. (Nujol): 2300, 1715, 1610 cm$^{-1}$.

The compounds described in Examples 2 to 22 were prepared according to the similar manner to that of Example 1.

Example 2

1-[3-{4-(4-Chlorobenzyl)-1-piperazinyl}propyl]isatin dihydrochloride (3.76 g) was obtained by reacting 1-(3-chloropropyl)isatin (2.98 g) with 1-(4-chlorobenzyl)piperazine (3.37 g), mp. 263° to 266° C. (dec.).

Example 3

1-[3-(4-Benzhydryl-1-piperazinyl)propyl]-5-chloroisatin dihydrochloride (1.91 g) was obtained by reacting 1-(3-chloropropyl)-5-chloroisatin (2.59 g) with 1-benzhydrylpiperazine (3.78 g), mp. 183° to 187° C. (dec.).

I.R. (Nujol): 3420, 3320, 2460, 1755, 1740, 1610 cm$^{-1}$.

Example 4

1-[3-(4-Benzhydryl-1-piperazinyl)propyl]-7-chloroisatin dihydrochloride (4.9 g) was obtaihed by reacting 1-(3-chloropropyl)-7-chloroisatin (3.87 g) with 1-benzhydrylpiperazine (5.04 g), mp. 243° C. (dec.).

I.R. (Nujol): 1740, 1605 cm$^{-1}$.

Example 5

1-[3-(4-Benzhydryl-1-piperazinyl)propyl]-5-fluoroisatin dihydrochloride (6.28 g) was obtained by reacting 1-(3-chloropropyl)-5-fluoroisatin (4.83 g) with 1-benzhydrylpiperazine (6.04 g), mp. 238° to 242° C. (dec.).

I.R. (Nujol): 2300, 1750, 1735, 1620 cm$^{-1}$.

Example 6

1-[3-(4-Benzhydryl-1-piperazinyl)propyl]-5-methylisatin dihydrochloride (5.33 g) was obtained by reacting 1-(3-chloropropyl)-5-methylisatin (4.76 g) with 1-benzhydrylpiperazine (7.56 g), mp. 231° to 234° C. (dec.).

I.R. (Nujol): 2400, 1745, 1740, 1625, 1605 cm$^{-1}$.

Example 7

1-[3-(4-Benzhydryl-1-piperazinyl)propyl]-7-methylisatin dihydrochloride (4.36 g) was obtained by reacting 1-(3-chloropropyl)-7-methylisatin (3.57 g) with 1-benzhydrylpiperazine (4.54 g), mp 257°-260° C.

I.R. (Nujol): 3450, 2400, 1745, 1610 cm$^{-1}$.

Example 8

1-[3-(4-Benzhydryl-1-piperazinyl)propyl]-5,7-dimethylisatin dihydrochloride (6.86 g) was obtained by reacting 1-(3-chloropropyl)-5,7-dimethylisatin (5.92 g) with 1-benzhydrylpiperazine (7.71 g), mp. 248.5° C. (dec.).

I.R. (Nujol): 1735, 1725, 1615, 1600 cm$^{-}$.

Example 9

1-[3-(4-Benzhydryl-1-piperazinyl)propyl]-5-chloro-7-methylisatin dihydrochloride (4.56 g) was obtained by reacting 1-(3-chloropropyl)-5-chloro-7-methylisatin (4.08 g) with 1-benzhydrylpiperazine (5.04 g), mp. 195° to 202° C. (dec.).

I.R. (Nujol): 3400, 2350, 1725, 1595 cm$^{-1}$.

Example 10

1-[3-(4-Benzhydryl-1-piperazinyl)propyl]-5-methoxyisatin dihydrochloride (3.28 g) was obtained by reacting 1-(3-chloropropyl)-5-methoxyisatin (4.32 g) with 1-benzhydrylpiperazine (6.43 g), mp. 237° to 240° C. (dec.).

Example 11

1-[3-(4-Benzhydryl-1-piperazinyl)propyl]-4-trifluoromethylisatin dihydrochloride (4.50 g) was obtained by reacting 1-(3-chloropropyl)-4-trifluoromethylisatin (2.92 g) with 1-benzhydrylpiperazine (3.02 g), mp. 201° to 204° C.

I.R. (Nujol): 3400, 2550, 1740, 1600 cm$^{-1}$.

Example 12

1-[3-(4-Benzhydryl-1-piperazinyl)propyl]-5-acetamidoisatin dihydrochloride (5.43 g) was obtained by reacting 1-(3-chloropropyl)-5-acetamidoisatin (4.2 g) with 1-benzhydrylpiperazine (5.62 g), mp. 226° C.

I.R. (Nujol): 1730, 1635 cm$^{-1}$.

Example 13

1-[3-(4-Benzhydryl-1-piperazinyl)propyl]-5-ethoxalylaminoisatin dihydrochloride (1.85 g) was obtained by reacting 1-(3-chloropropyl)-5-ethoxalylaminoisatin (2.38 g) with 1-benzhydrylpiperazine (2.12 g), mp. 248° C.

Example 14

1-[3-(4-Benzhydryl-1-piperazinyl)propyl]-5,7-dichloroisatin dihydrochloride (1.85 g) was obtained by reacting 1-(3-chloropropyl)-5,7-dichloroisatin (1.26 g) with 1-benzhydrylpiperazine (1.42 g), mp. 185° C. (dec.).

I.R. (Nujol): 3430, 2400, 1745, 1610 cm$^{-1}$.

Example 15

1-[3-(4-Benzhydryl-1-piperazinyl)propyl]-6,7-dimethylisatin dihydrochloride (1.26 g) was obtained by reacting 1-(3-chloropropyl)-6,7-dimethylisatin (1.11 g) with 1-benzhydrylpiperazine (1.44 g), mp. 259.5° C. (dec.).

I.R. (Nujol): 3450, 2400, 1735, 1610 cm$^{-1}$.

Example 16

1-[3-(4-Benzhydryl-1-piperazinyl)propyl]-4,7-dimethylisatin dihydrochloride (1.55 g) was obtained by reacting 1-(3-chloropropyl)-4,7-dimethylisatin (1.26 g) with 1-benzhydrylpiperazine (1.76 g), mp. 193° to 196° C. (dec.).

I.R. (Nujol): 3250, 2400, 1735, 1600 cm$^{-1}$.

Example 17

1-[3-(4-Benzhydryl-1-piperazinyl)-2-hydroxypropyl]isatin dihydrochloride.

I.R. (Nujol): 3300, 2525, 2300, 1740, 1615 cm$^{-1}$.

Example 18

1-[3-(1-Piperazinyl)propyl]isatin dihydrochloride.
I.R. (Nujol): 2700, 1735, 1620 cm$^{-1}$.

Example 19

1-[3-(4-Benzhydryl-1-piperazinyl)propyl]-4-morpholinoisatin trihydrochloride.

I.R. (Nujol): 3560, 3380, 2400, 1710, 1695, 1605 cm$^{-1}$.

Example 20

1-[3-(4-Benzhydryl-1-piperazinyl)propyl]-3-methoxyimino-2-indolinone dihydrochloride.

I.R. (Nujol): 2400, 1730, 1610 cm$^{-1}$.

Example 21

1-[3-(4-Benzhydryl-1-piperazinyl)propyl]-3-isobutoxyimino-2-indolinone dihydrochloride.

I.R. (Nujol): 3475, 1740, 1610 cm$^{-1}$.

Example 22

1-[3-(4-Benzhydryl-1-piperazinyl)propyl]-6-fluoroisatin dihydrochloride.

I.R. (Nujol): 3400, 2400, 1735, 1610 cm$^{-1}$.

Example 23

A mixture of 1-(5-bromopentyl)isatin (2.26 g), 1-benzhydrylpiperazine (2.5 g) and potassium carbonate (1.06 g) in N,N-dimethylformamide (18.5 ml) was stirred for 1.2 hours at 80° C. After cooling, the reaction mixture was poured into ice-water and stirred for a while. The precipitated crystals were collected by filtration, washed with water and then dried, followed by dissolving them (5.58 g) in ethanol (56 ml). To this solution was added ethanolic hydrogen chloride and concentrated to give a residue, which was washed with ethyl acetate by decantation. The residue was triturated with ethanol, collected by filtration, washed with ethanol and then dried. The resultant solid (3.19 g) was recrystallized from ethanol to give 1-[5-(4-benzhydryl-1-piperazinyl)pentyl]isatin dihydrochloride (1.30 g), mp. 226° to 226.5° C. (dec.).

I.R. (Nujol): 3500, 2300, 1745 (shoulder), 1735, 1615 cm$^{-1}$.

Example 24

1-[3-(4-Benzhydryl-1-piperazinyl)butyl]isatin dihydrochloride (1.05 g) was obtained by reacting 1-(3-bromobutyl)isatin (2.60 g) with 1-benzhydrylpiperazine (2.78 g) according to the similar manner to that of Example 23, mp. 249° to 250° C. (dec.).

I.R. (Nujol): 3400, 2350, 1725, 1610 cm$^{-1}$.

Example 25

A mixture of 1-(3-chloropropyl)isatin (2.24 g), 1-(4-chlorophenyl)piperazine (2.97 g), potassium carbonate (4.16 g) and potassium iodide (1.67 g) in N,N-dimethylformamide (23 ml) was stirred at ambient temperature for 40 minutes and then at 75° to 80° C. for 1.8 hours. After cooling, the reaction mixture was poured into a mixture of ice-water and ethyl acetate, followed by separating the organic layer. The remaining aqueous solution was extracted with ethyl acetate, and the combined extracts were washed with water and then dried over anhydrous magnesium sulfate. After removal of the solvent, the residue (4.56 g) was chromatographed on silica gel (50 g) using chloroform as an eluent. The fractions containing the object compound were collected and evaporated to give a residue (3.74 g), which was dissolved in a mixture of chloroform and ethanol. To this solution was added ethanolic hydrogen chloride, followed by stirring for a while. The precipitated solid was collected by filtration, washed with water and then dried to give 1-[3-{4-(4-chlorophenyl)-1-piperazinyl}propyl]isatin monohydrochloride (3.57 g), which was recrystallized from 90% ethanol to give the purified product (2.43 g) of the same compound, mp. 250° to 251° C. (dec.).

I.R. (Nujol): 2400, 1745, 1610 cm$^{-1}$.

Example 26

A mixture of 1-(4-bromobutyl)isatin (5.64 g), 1-benzhydrylpiperazine (7.56 g) and triethylamine (3.0 g) in N,N-dimethylformamide (48 ml) was stirred for 30 minutes at 80° C. The reaction mixture was poured into ice-water and extracted with ethyl acetate. The extract was washed with water, dried over anhydrous magnesium sulfate and then evaporated. The residue was subjected to column chromatography on silica gel (50 g) using chloroform as an eluent. The fractions containing the object compound were collected and evaporated. The remaining oil (3.25 g) was crystallized from diisopropyl ether, washed with diethyl ether, and then recrystallized from acetonitrile to give crystals of 1-[4-(4-benzhydryl-1-piperazinyl)butyl]isatin (2.69 g), mp. 127° to 129° C.

I.R. (Nujol): 1745, 1610 cm$^{-1}$.

Example 27

1-[2-(4-Benzhydryl-1-piperazinyl)ethyl]isatin (1.58 g) was obtained by reacting 1-(2-bromoethyl)isatin (3.81 g) with 1-benzhydrylpiperazine (5.04 g) according to the similar manner to that of Example 26, mp. 145° to 147.5° C.

I.R. (Nujol): 1750, 1740, 1610 cm$^{-1}$.

Example 28

A mixture of 1-(4-bromobutyl)-5-methylisatin (2.96 g), 1-benzhydrylpiperazine (2.77 g) and potassium carbonate (1.39 g) in N,N-dimethylformamide (24 ml) was stirred at 80° C. for half an hour. After cooling, the reaction mixture was poured into ice-water with stirring, followed by stirring for a while. The precipitated solid was collected by filtration, washed with water and then dried to give a residue (5.37 g), which was recrystallized from acetonitrile to give 1-[4-(4-benzhydryl-1-piperazinyl)butyl]-5-methylisatin (2.62 g). These crystals were recrystallized again from the same solvent to give the purified product (2.37 g) of the same compound, mp. 149.5° to 150.5° C.

I.R. (Nujol): 1740, 1620, 1600 cm$^{-1}$.

The compounds described in Examples 29 to 34 were prepared according to the similar manner to that of Example 28.

Example 29

1-[4-(4-Benzhydryl-1-piperazinyl)butyl]-5-fluoroisatin (2.15 g) was obtained by reacting 1-(4-bromobutyl)-5-fluoroisatin (2.5 g) with 1-benzhydrylpiperazine (2.31 g), mp. 143.5° to 144.5° C.

I.R. (Nujol): 1750 (shoulder), 1740, 1620 1610 cm$^{-1}$.

Example 30

1-[4-(4-Benzhydryl-1-piperazinyl)butyl]-5-bromoisatin (1.32 g) was obtained by reacting 1-(4-bromobutyl)-5-bromoisatin (1.45 g) with 1-benzhydrylpiperazine (1.16 g), mp. 132° to 133° C.

I.R. (Nujol): 1745, 1610 cm$^{-1}$.

Example 31

1-[3-(4-Benzhydryl-1-piperazinyl)propyl]-6-chloroisatin.

I.R. (Nujol): 3650, 1740 (shoulder), 1730, 1600 cm$^{-1}$.

Example 32

1-[3-(4-Benzhydryl-1-piperazinyl)propyl]-4-chlorisatin.

I.R. (Nujol): 1745, 1600 cm$^{-1}$.

Example 33

1-[3-{4-(10,11-Dihydro-5H-dibenzo[a,d]cyclohepten-5-yl)-1-piperazinyl}propyl]isatin.

I.R. (Nujol): 1720, 1610 cm$^{-1}$.

Example 34

1-[3-{4-(N,N-Diphenylcarbamoyl)-1-piperazinyl}-propyl]isatin.

I.R. (Nujol): 1740, 1625, 1610 cm$^{-1}$.

Example 35

A mixture of 1-(3-chloropropyl)benz[g]isatin (1.3 g), 1-benzhydrylpiperazine (1.68 g), potassium carbonate (0.66 g) and potassium iodide (0.79 g) in dry N,N-dimethylformamide (11 ml) was stirred for 5 hours at 80° C. After cooling, the reaction mixture was poured into a mixture of ice-water and ethyl acetate, followed by separating out the organic layer. The remaining aqueous layer was extracted with ethyl acetate, and the extract and the organic layer previously obtained were combined, washed with water and then dried over anhydrous magnesium sulfate. After removal of the solvent, the residue (3 g) was chromatographed on silica gel (45 g) using chloroform as an eluent to give an oil, which was crystallized from ethanol to obtain 1-[3-(4-benzhydryl-1-piperazinyl)propyl]benz[g]isatin (0.93 g). This product was recrystallized from ethanol to give the purified product (0.73 g) of the same compound, mp. 134.5°–135.5° C.

I.R. (Nujol): 1750, 1725, 1620, 1595 cm$^{-1}$.

The compounds described in Examples 36 and 37 were prepared according to the similar manner to that of Example 35.

Example 36

1-[3-(4-Trityl-1-piperazinyl)propyl]isatin (3.68 g) was obtained by reacting 1-(3-chloropropyl)isatin (2.24 g) with 1-tritylpiperazine (3.89 g), mp. 145° to 149° C.

I.R. (Nujol): 1740, 1620 cm$^{-1}$.

Example 37

1-[3-{4-(3-Chlorophenyl)-1-piperazinyl}propyl]isatin (1.80 g) was obtained by reacting 1-(3-chloropropyl)isatin (2.24 g) with 1-(3-chlorophenyl)piperazine (2.5 g), mp. 152.5° to 153.5° C.

I.R. (Nujol): 1735, 1605 cm$^{-1}$.

Example 38

A mixture of isatin (1.32 g) and 50% sodium hydride (0.44 g) in N,N-dimethylformamide (13 ml) was stirred for 10 minutes at ambient temperature. To the mixture was added a solution of 4-benzhydryl-1-(3-chloropropyl)piperazine (3.04 g) in N,N-dimethylformamide (6 ml) and the mixture was stirred for 2.5 hours at 50° to 60° C. The reaction mixture was poured into water (150 ml) and extracted with ethyl acetate. The extract was washed with water, dried over anhydrous magnesium sulfate and evaporated to dryness. To the residue dissolved in ethanol (30 ml) was added 29% ethanolic hydrogen chloride (6 ml), followed by an addition of diethyl ether (20 ml). The resulting precipitate was filtered and recrystallized from a mixture of methanol and diethyl ether to give crystals of 1-[3-(4-benzhydryl-1-piperazinyl)propyl]isatin dihydrochloride (1.31 g), mp. 245° to 248° C. (dec.).

Example 39

1-[3-(4-Benzhydryl-1-piperazinyl)propyl]-5-chloroisatin (0.29 g) was obtained by reacting 5-chloroisatin (0.48 g) with 4-benzhydryl-1-(3-chloropropyl)piperazine (0.87 g) according to the similar manner to that of Example 38, mp. 178° to 182° C. (dec.).

Example 40

To a suspension of 6-chloroisatin (2 g) in dry N,N-dimethylformamide (12 ml) was added at a time potassium tert-butoxide (1.52 g) under ice-cooling and the mixture was stirred at ambient temperature for 20 minutes. To this mixture was added dropwise a solution of 4-benzyhydryl-1-(3-chloropropyl)piperazine (4.35 g) in dry N,N-dimethylformamide (5 ml) with stirring over a period of 10 minutes, and the stirring was continued at ambient temperature for 45 minutes and at 60° to 70° C. for additional 4.3 hours. After cooling, the reaction mixture was poured into a mixture of ice-water and ethyl acetate, followed by separating out the ethyl acetate layer. The remaining aqueous solution was further extracted with ethyl acetate, and the combined extracts were washed with water, dried over anhydrous magnesium sulfate and then evaporated to dryness to give a residue (5.61 g), which was treated with diisopropyl ether. The resultant residue (3 g) was chromatographed on silica gel (30 g) using a mixed solvent of chloroform and methanol (9:1 by volume) and the fractions containing the object compound were collected and evaporated to dryness to give crude crystals of 1-[3-(4-benzhydryl-1-piperazinyl)propyl]-6-chloroisatin (1.06 g). Recrystallization from ethanol gave the purified product (0.78 g) of the same compound, mp. 124° to 127° C.

I.R. (Nujol): 3650, 1740 (shoulder), 1730, 1600 cm$^{-1}$.

The compounds described in Examples 41 and 42 were obtained according to the similar manner to that of Example 40.

Example 41

1-[3-(4-Benzhydryl-1-piperazinyl)propyl]-4-chlorisatin (2.30 g) was obtained by reacting 4-chloroisatin (2 g) with 4-benzhydryl-1-(3-chloropropyl)piperazine (4.35 g), mp. 142° to 143° C.

I.R. (Nujol): 1745, 1600 cm$^{-1}$.

Example 42

1-[3-(4-Benzhydryl-1-piperazinyl)propyl]-6-fluoroisatin dihydrochloride (2.25 g) was obtained by reacting 6-fluoroisatin (3.3 g) with 4-benzhydryl-1-(3-chloropropyl)isatin (8.1 g), mp. 89° to 98° C.

I.R. (Nujol): 3400, 2400, 1735, 1610 cm$^{-1}$.

Example 43

To a suspension of isatin (2.22 g) in dry N,N-dimethylformamide (30 ml) was added at a time potassium tert-butoxide (2.07 g) under ice-water cooling with stirring, and the stirring was continued at ambient temperature for 20 minutes. To this mixture was added dropwise a suspension of 1-(4-benzhydryl-1-piperazinyl)-3-chloropropan-2-ol (5.73 g) in N,N-dimethylformamide (15 ml) with stirring over a period of 10 minutes, followed by adding at a time potassium iodide (0.51 g). After the stirring was continued at 60° to 70° C. for 6 hours, the reaction mixture was poured into a mixture of ice-water and ethyl acetate, followed by separating out the ethyl acetate layer. The remaining aqueous solution was extracted with ethyl acetate, and the combined extracts were washed with water, dried over anhydrous magnesium sulfate and then evaporated to dryness. The residue (7.69 g) was chromatographed on silica gel (80 g) using chloroform as an eluent, and the fractions containing a desired compound were collected and evaporated to dryness to give a residue (3.2 g), which was dissolved in diethyl ether. To this solution was added ethanolic hydrogen chloride and the precipitated crystals were collected by filtration to give 1-[3-(4-benzhydryl-1-piperazinyl)-2-hydroxypropyl]isatin dihydrochloride (3.37 g), which was recrystallized from 90% ethanol to obtain the purified product (0.43 g) of the same compound, mp. 242° to 243° C. (dec.).

I.R. (Nujol): 3300, 2525, 2300, 1740, 1615 cm$^{-1}$.

The compounds described in Examples 44 to 71 were prepared according to the similar manner to that of Example 43.

Example 44

1-[3-{4-(4-Chlorobenzyl)-1-piperazinyl}propyl]isatin dihydrochloride, mp. 263° to 266° C. (dec.).

Example 45

1-[3-(4-Benzyhydryl-1-piperazinyl)propyl]-7-chloroisatin dihydrochloride.

I.R. (Nujol): 1740, 1605 cm$^{-1}$.

Example 46

1-[3-(4-Benzhydryl-1-piperazinyl)propyl]-5-fluoroisatin dihydrochloride.

I.R. (Nujol): 2300, 1750, 1735, 1620 cm$^{-1}$.

Example 47

1-[3-(4-Benzhydryl-1-piperazinyl)propyl]-5-methylisatin dihydrochloride.

I.R. (Nujol): 2400, 1745, 1740, 1625, 1605 cm$^{-1}$.

Example 48

1-[3-(4-Benzhydryl-1-piperazinyl)propyl]-7-methylisatin dihydrochloride.

I.R. (Nujol): 3450, 2400, 1745, 1610 cm$^{-1}$.

Example 49

1-[3-(4-Benzhydryl-1-piperazinyl)propyl]-5,7-dimethylisatin dihydrochloride.

I.R. (Nujol): 1735, 1725, 1615, 1600 cm$^{-1}$.

Example 50

1-[3-(4-Benzhydryl-1-piperazinyl)propyl]-5-chloro-7-methylisatin dihydrochloride I.R. (Nujol): 3400, 2350, 1725, 1595 cm$^{-1}$.

Example 51

1-[3-(4-Benzhydryl-1-piperazinyl)propyl]-5-methoxyisatin dihydrochloride, mp. 237° to 240° C. (dec.).

Example 52

1-[3-(4-Benzhydryl-1-piperazinyl)propyl]-4-trifluoromethylisatin dihydrochloride.

I.R. (Nujol): 3400, 2550, 1740, 1600 cm$^{-1}$.

Example 53

1-[3-(4-Benzhydryl-1-piperazinyl)propyl]-5-acetamidoisatin dihydrochloride.

I.R. (Nujol): 1730, 1635 cm$^{-1}$.

Example 54

1-[3-(4-Benzhydryl-1-piperazinyl)propyl]-5-ethoxalylaminoisatin dihydrochloride, mp. 248° C.

Example 55

1-[3-(4-Benzhydryl-1-piperazinyl)propyl]-5,7-dichloroisatin dihydrochloride.

I.R. (Nujol): 3430, 2400, 1745, 1610 cm$^{-1}$.

Example 56

1-[3-(4-Benzhydryl-1-piperazinyl)propyl]-6,7-dimethylisatin dihydrochloride.

I.R. (Nujol): 3450, 2400, 1735, 1610 cm$^{-1}$.

Example 57

1-[3-(4-Benzhydryl-1-piperazinyl)propyl]-4,7-dimethylisatin dihydrochloride.

I.R. (Nujol): 3250, 2400, 1735, 1600 cm$^{-1}$.

Example 58

1-[3-(1-Piperazinyl)propyl]isatin dihydrochloride.

I.R. (Nujol): 2700, 1735, 1620 cm$^{-1}$.

Example 59

1-[3-(4-Benzhydryl-1-piperazinyl)propyl]-3-methoxyimino-2-indolinone dihydrochloride.

I.R. (Nujol): 2400, 1730, 1610 cm$^{-1}$.

Example 60

1-[3-(4-Benzhydryl-1-piperazinyl)propyl]-3-isobutoxyimino-2-indolinone dihydrochloride.

I.R. (Nujol): 3475, 1740, 1610 cm$^{-1}$.

Example 61

1-[5-(4-Benzhydryl-1-piperazinyl)pentyl]isatin.

I.R. (Nujol): 3500, 2300, 1745 (shoulder), 1735, 1615 cm$^{-1}$.

Example 62

1-[3-{4-(4-Chlorophenyl)-1-piperazinyl}propyl]isatin monohydrochloride.

I.R. (Nujol): 2400, 1745, 1610 cm$^{-1}$.

Example 63

1-[4-(4-Benzhydryl-1-piperazinyl)butyl]isatin.

I.R. (Nujol): 1745, 1610 cm$^{-1}$.

Example 64

1-[2-(4-Benzhydryl-1-piperazinyl)ethyl]isatin.

I.R. (Nujol): 1750, 1740, 1610 cm$^{-1}$.

Example 65

1-[4-(4-Benzhydryl-1-piperazinyl)butyl]-5-methylisatin.

I.R. (Nujol): 1740, 1620, 1600 cm$^{-1}$.

Example 66

1-[4-(4-Benzhydryl-1-piperazinyl)butyl]-5-fluoroisatin.

I.R. (Nujol): 1750, 1740, 1620, 1610 cm$^{-1}$.

Example 67

1-[4-(4-Benzhydryl-1-piperazinyl)butyl]-5-bromisatin.

I.R. (Nujol): 1745, 1610 cm$^{-1}$.

Example 68

1-[3-(4-Benzhydryl-1-piperazinyl)butyl]isatin.
I.R. (Nujol): 3430, 2350, 1725, 1610 cm$^{-1}$.

Example 69

1-[3-{4-(10,11-Dihydro-5H-dibenzo[a,d]cyclohepten-5-yl)-1-piperazinyl}propyl]isatin.
I.R. (Nujol): 1720, 1610 cm$^{-1}$.

Example 70

1-[3-{4-(N,N-Diphenylcarbamoyl)-1-piperazinyl}-propyl]isatin.
I.R. (Nujol): 1740, 1625, 1610 cm$^{-1}$.

Example 71

1-[3-(4-Benzhydryl-1-piperazinyl)propyl]-4-morpholinoisatin trihydrochloride.
I.R. (Nujol): 3560, 3380, 2400, 1710, 1695, 1605 cm$^{-1}$.

Example 72

A mixture of 1-[3-(4-benzhydryl-1-piperazinyl)-propyl]isatin (1.81 g) and O-methylhydroxylamine hydrochloride (420 mg) in methanol (36 ml) was stirred for an hour at ambient temperature. After addition of 29% ethanolic hydrogen chloride (2 ml), the reaction mixture was evaporated to dryness. The residue was triturated with ethanol and then recrystallized from 90% ethanol to give pale yellow crystals of 1-[3-(4-benzhydryl-1-piperazinyl)propyl]-3-methoxyimino-2-indolinone dihydrochloride (1.65 g), mp. 191° to 196° C.
I.R. (Nujol): 2400, 1730, 1610 cm$^{-1}$.

Example 73

1-[3-(4-Benzhydryl-1-piperazinyl)propyl]-3-isobutoxyimino-2-indolinone dihydrochloride (2.00 g) was obtained by reacting 1-[3-(4-benzhydryl-1-piperazinyl)-propyl]isatin dihydrochloride (2 g) with O-isobutylhydroxylamine hydrochloride (0.59 g) in the presence of potassium carbonate (1.62 g) in 90% ethanol in substantially the same manner as that of Example 72, mp. 227.5° to 228° C.
I.R. (Nujol): 3475, 1740, 1610 cm$^{-1}$.

Example 74

To a solution of 1-[3-(4-trityl-1-piperazinyl)propyl]isatin (5.0 g) in tetrahydrofuran (100 ml) was added all at once concentrated hydrochloric acid (5 ml) and the mixture was vigorously stirred for half an hour. The resultant precipitates were collected by filtration and washed with tetrahydrofuran to give 1-[3-(1-piperazinyl)propyl]isatin dihydrochloride (2.96 g).
I.R. (Nujol): 2700, 1735, 1620 cm$^{-1}$.

Example 75

To a suspension of 1-[3-(1-piperazinyl)propyl]isatin dihydrochloride (1.39 g) in N,N-dimethylformamide (20 ml) was added diazabicyclo[5,4,0]undecene-5 (1.22 g) and the mixture was stirred for a while. Methyl 2-bromo-2-phenylacetate (1.15 g) was added thereto and the stirring was continued at ambient temperature for 5 hours. After pouring the reaction mixture into a mixture of ethyl acetate and water, the ethyl acetate layer was separated and washed with water and then dried over anhydrous magnesium sulfate. After the solvent was removed under reduced pressure, the resultant oil (1.80 g) was chromatographed on silica gel (20 g) using chloroform as an eluant and the fractions containing the object component were collected. Removal of the solvent gave an oil (0.60 g), which was dissolved in methanol. To this solution was added ethanolic hydrogen chloride and evaporated. The residue was crystallized from chloroform and then recrystallized from the same solvent to give methyl 2-[4-{3-(isatin-1-yl)propyl}-1-piperazinyl]-2-phenylacetate dihydrochloride (0.31 g).
I.R. (Nujol): 3400, 2400, 1720, 1615 cm$^{-1}$.

Example 76

To a suspension of 1-[3-(1-piperazinyl)propyl]isatin dihydrochloride (2.78 g) in methylene chloride (52 ml) was added bis(trimethylsilyl)acetamide (5.06 g), and the mixture was stirred for half an hour. After 5-chloro-10,11-dihydro-5H-dibenzo[a,d]cycloheptene (2.76 g) was added thereto, the stirring was continued at ambient temperature for 5 hours. The reaction mixture was poured into water and then the organic layer was separated out, washed with water and dried over anhydrous magnesium sulfate. After removal of the solvent, the residue was pulverized with diethyl ether to give the solid (2.01 g), which was chromatographed on silica gel (40 g) using chloroform and then a mixture of chloroform and methanol (99:1 by volume). Fractions containing a desired component were collected and the solvent was removed to give a residue (1.01 g) which was recrystallized from ethanol to obtain 1-[3-{4-(10,11-dihydro-5H-dibenzo[a,d]cyclohepten-5-yl}-1-piperazinyl}-propyl]isatin (0.98 g), mp 159°-161.5° C.
I.R. (Nujol): 1720, 1610 cm$^{-1}$.

Example 77

To a suspension of 1-[3-(1-piperazinyl)propyl]isatin dihydrochloride (1.39 g) in methylene chloride (40 ml) was added bis(trimethylsilyl)acetamide (3.44 g), and the mixture was stirred for 10 minutes. After N,N-diphenylcarbamoyl chloride (1.16 g) was added thereto, the stirring was continued at the ambient temperature for 5 hours. The reaction mixture was poured into ice-water and the methylene chloride layer was separated, washed with water and then dried over anhydrous magnesium sulfate. After removal of the solvent, the residue was crystallized from diethyl ether to obtain N,N-diphenyl-4-[3-(isatin-1-yl)propyl]piperazine-1-carboxamide (0.62 g), mp. 163° to 164.5° C.
I.R. (Nujol): 1740, 1625, 1610 cm$^{-1}$.

Example 78

A mixture of 1-[3-(4-benzhydryl-1-piperazinyl)-propyl]-4-chloroisatin dihydrochloride (4.20 g), morpholine (1.09 g), potassium carbonate (3.18 g) and potassium iodide (0.33 g) in N,N-dimethylformamide (42 ml) was stirred at 80° C. for 5.5 hours. After the reaction mixture was cooled to 15° C., it was poured into water and extracted with chloroform. The extract was washed with water and then dried over anhydrous magnesium sulfate. Removal of the solvent gave an oil, which was chromatographed on silica gel (100 g) using chloroform as an eluent. The fractions containing the object compound were collected and evaporated to give an oil (4.03 g), which was dissolved in ethanol (50 ml). Thereto was added 20% ethanolic hydrogen chloride (4.5 ml), followed by stirring for a while. The precipitating crystals were collected by filtration, washed with ethanol and recrystallized from 90% ethanol to give 1-[3-(4-benzhydryl-1-piperazinyl)propyl]-4-morpholinoisatin trihydrochloride (1.09 g), mp. 201°-203° C.

I.R. (Nujol): 3560, 3380, 2400, 1710, 1695, 1605 cm$^{-1}$.

Example 79

To a suspension of 1-[3-(4-benzhydryl-1-piperazinyl)propyl]isatin (2 g) in dry methanol (15 ml) was added at a time a solution of methyl iodide (4.54 g) in dry methanol (7 ml), and the mixture was refluxed under heating for 4.3 hours. After cooling, the precipitated solid was collected by filtration, washed with methanol and then dried. This solid (2.42 g) was recrystallized from 70% ethanol to give methyl iodide salt of 1-[3-(4-benzhydryl-1-piperazinyl)propyl]isatin (1.70 g), mp. 242.5°–243° C.

I.R. (Nujol): 1740 (shoulder), 1730 (shoulder), 1725, 1605 cm$^{-1}$.

PREPARATION OF THE STARTING COMPOUNDS

Preparation 1

To a solution of isatin (14.7 g) in N,N-dimethylformamide (150 ml) was added potassium tert-butoxide (13.95 g) under cooling at 5° C., and the mixture was stirred vigorously for about 10 minutes. To the mixture was added dropwise a solution of 1-bromo-3-chloropropane (17.35 g) in N,N-dimethylformamide (50 ml) over a period of about 30 minutes at ambient temperature, and the mixture was stirred for 5 hours at the same temperature. The reaction mixture was poured into a mixture of ethyl acetate (300 ml) and ice-water (500 ml) containing 50 ml of 10% hydrochloric acid. After separation of the ethyl acetate layer, the aqueous layer was further extracted with ethyl acetate. The ethyl acetate layers were combined, washed with water, dried over anhydrous magnesium sulfate and then evaporated. The residue was subjected to column chromatography on silica gel (100 g) using chloroform as an eluent. The fractions containing the object compound were collected, and concentrated to give crystals of 1-(3-chloropropyl)isatin (19.68 g), mp. 72°–76.5° C.

I.R. (Nujol): 1745 (shoulder), 1735, 1610 cm$^{-1}$.

The compounds described in Preparations 2 to 17 were prepared by reacting the corresponding istation compounds (II) with 1-bromo-3-chloropropane according to the similar manner to that of Preparation 1.

Preparation 2

1-(3-Chloropropyl)-5-chloroisatin, mp. 131° to 135.5° C.

I.R. (Nujol): 1750, 1610 cm$^{-1}$.

Preparation 3

1-(3-Chloropropyl)-7-chloroisatin, mp. 117° to 122° C.

I.R. (Nujol): 1735, 1600 cm$^{-1}$.

Preparation 4

1-(3-Chloropropyl)-5-fluoroisatin, mp. 106° to 109° C.
I.R. (Nujol): 1760, 1755 (shoulder), 1625, 1610 cm$^{-1}$.

Preparation 5

1-(3-Chloropropyl)-6-fluoroisatin, mp. 88° to 91° C.
I.R. (Nujol): 1740, 1620, 1605 cm$^{-1}$.

Preparation 6

1-(3-Chloropropyl)-5-methylisatin, mp. 90° to 94.5° C.

I.R. (Nujol): 1745, 1625, 1605 cm$^{-1}$.

Preparation 7

1-(3-Chloropropyl)-7-methylisatin, mp. 151° to 154° C.

I.R. (Nujol): 1750, 1740, 1610 (shoulder), 1600 cm$^{-1}$.

Preparation 8

1-(3-Chloropropyl)-5,7-dimethylisatin, mp. 125° to 135° C.
I.R. (Nujol): 1730, 1615, 1600 cm$^{-1}$.

Preparation 9

1-(3-Chloropropyl)-5-chloro-7-methylisatin, mp. 74° to 77° C.

I.R. (Nujol): 1740, 1730, 1610 cm$^{-1}$.

Preparation 10

1-(3-Chloropropyl)-5-methoxyisatin, mp. 102° to 105° C.

I.R. (Nujol): 1740, 1730, 1620, 1610 cm$^{-1}$.

Preparation 11

1-(3-Chloropropyl)-4-trifluoromethylisatin, mp. 114° to 116.5° C.
I.R. (Nujol): 1760 (shoulder), 1745, 1600 cm$^{-1}$.

Preparation 12

1-(3-Chloropropyl)-5-acetamidoisatin, mp. 170° to 172° C.

I.R. (Nujol): 3340, 1740, 1730, 1695, 1620, 1600 cm$^{-1}$.

Preparation 13

1-(3-Chloropropyl)-5-ethoxyalylaminoisatin, mp. 176° to 180° C.

I.R. (Nujol): 3290, 1765, 1740, 1710 cm$^{-1}$.

Preparation 14

1-(3-Chloropropyl)-5,7-dichloroisatin, mp. 103° to 105° C.

I.R. (Nujol): 1750, 1605 cm$^{-1}$.

Preparation 15

1-(3-Chloropropyl)-6,7-dimethylisatin, mp. 141.5° to 146.5° C.

I.R. (Nujol): 1735, 1605 cm$^{-1}$.

Preparation 16

1-(3-Chloropropyl)-4,7-dimethylisatin, mp. 70° to 71° C.

I.R. (Nujol): 1730, 1595 cm$^{-1}$.

Preparation 17

1-(3-Chloropropyl)benz[g]isatin, mp. 130° to 143° C.
I.R. (Nujol): 1750 (shoulder), 1735, 1620, 1600 cm$^{-1}$.

Preparation 18

To a solution of isatin (7.35 g) in N,N-dimethylformamide (70 ml) was added potassium tert-butoxide (6.98 g) under cooling at 5° C., and the reaction mixture was stirred for 10 minutes at the same temperature. To the mixture was added dropwise a solution of 1,4-dibromobutane (54 g) in N,N-dimethylformamide (25 ml), and stirred for an hour at 18° C. The reaction mixture was poured into ice-water, and extracted with chloroform. The extracts were combined, washed with water and evaporated. After addition of n-hexane (200 ml) to the residue, the solvent was decanted and then to the residue was added chloroform (20 ml). The mixture was filtered to remove insoluble substances and the filtrate was subjected to column chromatography on silica gel (50 g), eluted with chloroform. The fractions containing the object compound were collected, and concentrated to give dark red oil of 1-(4-bromobutyl)isatin (7.52 g).

I.R. (CHCl$_3$): 1750, 1615 cm$^{-1}$.

The compounds described in Preparations 19 to 24 were prepared by reacting the correponding isatin compounds (II) with the corresponding dibromoalkane according to the similar manner to that of Preparation 18.

Preparation 19

1-(2-Bromoethyl)isatin, mp. 130° to 130.5° C.
I.R. (Nujol): 1745, 1610 cm$^{-1}$.

Preparation 20

1-(3-Bromobutyl)isatin, mp. 74° to 76° C.
I.R. (Nujol): 1750, 1730 (shoulder), 1610 cm$^{-1}$.

Preparation 21

1-(4-Bromobutyl)-5-methylisatin, mp. 115° to 118° C.
I.R. (Nujol): 1745, 1620, 1600 cm$^{-1}$.

Preparation 22

1-(4-Bromobutyl)-5-fluoroisatin, mp. 94° to 99° C.
I.R. (Nujol): 1755, 1735, 1625, 1610 cm$^{-1}$.

Preparation 23

1-(5-Bromopentyl)isatin.
I.R. (Film): 1745, 1615 cm$^{-1}$.

Preparation 24

1-(4-Bromobutyl)-5-bromoisatin, mp. 92° to 93° C.
I.R. (KBr): 1745, 1605 cm$^{-1}$.

Preparation 25

A mixture of 1-benzhydrylpiperazin (4.13 g), 1-bromo-3-chloropropane (5.18 g) and anhydrous potassium carbonate (2.26 g) in anhydrous acetone (82 ml) was refluxed for 10 hours under stirring. The insoluble materials were filtered off and the filtrate was evaporated to dryness. The residue was subjected to column chromatography on alumina (50 g) using benzene as an eluent. The fractions containing the object compound were collected and evaporated to give oil of 1-benzhydryl-4-(3-chloropropyl)piperazine (3.04 g).

I.R. (Film): 1600, 1450, 1280, 1130, 1000 cm$^{-1}$.

What we claim is:

1. A compound of the formula:

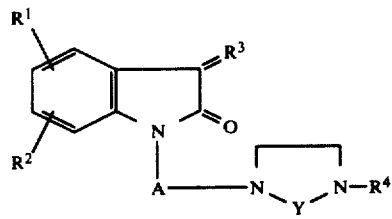

wherein $R^1$ and $R^2$ are each hydrogen, halogen, lower alkyl, lower alkoxy, halo (lower) alkyl, lower alkanoylamino, lower alkoxalylamino, or a 5 to 6 membered saturated or unsaturated heterocyclic group having at least one imino group, and selected from the group consisting of pyrrolidinyl, pyrrolinyl, imidazolidinyl, piperazinyl, piperidyl, and morpholynyl, or $R^1$ and $R^2$ are combined together to form a benzene ring, $R^3$ is oxo or a group of the formula =N—OR$^5$, in which $R^5$ is hydrogen or lower alkyl, $R^4$ is mono- or di- or triphenyl (lower) alkyl, A is $C_1$ to $C_7$ alkylene and its hydroxy derivatives, Y is ($C_1$ to $C_3$) alkylene, and a pharmaceutically acceptable salt thereof.

2. The compound according to claim 1, wherein $R^3$ is oxo and Y is ethylene.

3. The compound according to claim 2, wherein $R^4$ is mono- or di- or tri-phenyl(lower)alkyl having halogen or lower alkoxycarbonyl on the phenyl ring.

4. The compound according to claim 3, wherein $R^4$ is benzhydryl.

5. The compound according to claim 4, that is 1-[3-(4-benzhydryl-1-piperazinyl)propyl]isatin and its dihydrochloride.

6. The compound according to claim 4, that is 1-[4-(4-benzhydryl-1-piperazinyl)butyl]isatin and its dihydrochloride.

7. The compound according to claim 4, that is 1-[3-(4-benzhydryl-1-piperazinyl)butyl]isatin and its dihydrochloride.

8. The compound according to claim 4, that is 1-[5-(4-benzhydryl-1-piperazinyl)pentyl]isatin and its dihydrochloride.

9. The compound according to claim 4, that is 1-[3-(4-benzhydryl-1-piperazinyl)propyl]-4-chloroisatin and its dihydrochloride.

10. The compound according to claim 4, that is 1-[3-(4-benzhydryl-1-piperazinyl)propyl]-5-chloroisatin and its dihydrochloride.

11. The compound according to claim 4, that is 1-[3-(4-benzhydryl-1-piperazinyl)propyl]-5-fluoroisatin and its dihydrochloride.

12. The compound according to claim 4, that is 1-[3-(4-benzhydryl-1-piperazinyl)propyl]-5-methoxyisatin and its dihydrochloride.

13. The compound according to claim 1, wherein $R^4$ is trityl.

14. The compound according to claim 2, wherein $R^4$ is hydrogen, phenyl optionally having halogen, N,N-diphenylcarbomoyl or 10,11-dihydro-5H-dibenzo[a,d]cycloheptenyl.

15. The compound according to claim 1, wherein $R^3$ is a group of the formula: =N—OR$^5$, in which $R^5$ is lower alkyl, and Y is ethylene.

16. An antiallergic composition comprising, as an active ingredient, the compound of claim 1, in association with a non-toxic, pharmaceutically acceptable in sufficient amount to provide antiallergic properties carrier.

* * * * *